United States Patent [19]

Brunnmueller et al.

[11] Patent Number: 4,687,848

[45] Date of Patent: Aug. 18, 1987

[54] PREPARATION OF 2-AMINOPYRAZINES AND PYRAZINES

[75] Inventors: Fritz Brunnmueller, Limburgerhof; Michael Kroener, Mannheim, both of Fed. Rep. of Germany

[73] Assignee: BASF Aktiengesellschaft, Ludwigshafen, Fed. Rep. of Germany

[21] Appl. No.: 740,435

[22] Filed: Jun. 3, 1985

Related U.S. Application Data

[62] Division of Ser. No. 547,852, Nov. 2, 1983, Pat. No. 4,560,756.

[30] Foreign Application Priority Data

Nov. 15, 1982 [DE] Fed. Rep. of Germany ....... 3242195

[51] Int. Cl.$^4$ .................. C07D 241/18; C07D 241/20
[52] U.S. Cl. .................................. 544/336; 544/408; 544/409
[58] Field of Search ..................... 544/336, 408, 409

[56] References Cited

U.S. PATENT DOCUMENTS 3,607,910  9/1971  Wood et al. ...................... 560/171

OTHER PUBLICATIONS

Chem. Ber. 100 (1967) 560–563.
J. Amer. Chem. Soc. 90 (1968) 2424, 2425.
J. Org. Chem. 44 (1979) 1128–1130.
Barot et al., J. Chem. Soc. Perkin I, (1973) 606–612.
Chem. Abstracts, vol. 91 (1979) Entry 57537p.

*Primary Examiner*—Robert Gerstl
*Assistant Examiner*—William A. Teoli, Jr.
*Attorney, Agent, or Firm*—John H. Shurtleff

[57] ABSTRACT

Novel 2-aminopyrazines and processes for the preparation of 2-aminopyrazines and pyrazines by reaction of an α-iminodiacetonitrile (a) with a hydrogen halide or (b) with an alcohol or a thioalcohol and a hydrogen halide or (c) with an alcohol or a thioalcohol in the presence of an alkali metal compound and/of an alkaline earth metal compound. The 2-aminopyrazines and pyrazines obtainable by the process of the invention are useful starting materials for the preparation of dyes, fungicides, bactericides, textile assistants, scents, folic acid derivatives, flavorings, and active ingredients in crop protection and drugs.

8 Claims, No Drawings

PREPARATION OF 2-AMINOPYRAZINES AND PYRAZINES

This application is a division of application Ser. No. 547,852, filed Nov. 2, 1983, now U.S. Pat. No. 4,560,756.

The present invention relates to novel 2-aminopyrazines and to a process for the preparation of 2-aminopyrazines and pyrazines by reacting an -iminodiacetonitrile (a) with a hydrogen halide or (b) with an alcohol or a thioalcohol in the presence of an alkali metal compound/or an alkaline earth metal compound.

2-Aminopyrazines which are unsubstituted or substituted in the 5-position are prepared by condensation of a 1,2-dicarbonyl compound with a dihydrobromide of aminoacetamidine in the presence of a base, in methanol, at $-30°$ C. (Pitre and Boveri, Chem. Ber. 100 (1967), 560–563):

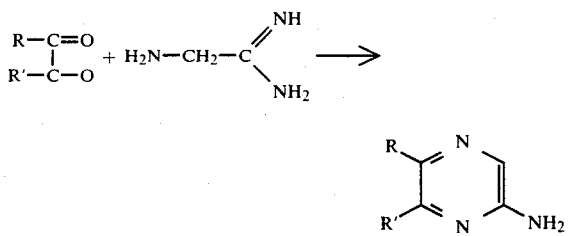

3,5-Disubstituted 2-aminopyrazine-1-oxides are obtained (J. Amer. Chem. Soc. 90 (1968), 2424 and 2425) by condensation of an oximinoketone with an α-aminonitrile in glacial acetic acid at room temperature:

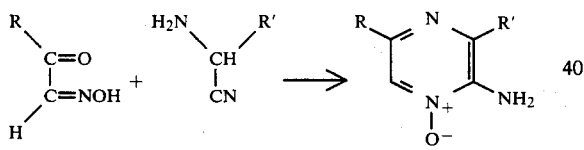

The oximino compounds are difficult to obtain.

Vohra et al. (J. Org. Chem. 44 (1979), 1128–1130) describe the reaction of α-iminodiacetonitrile with sulfuric acid and sodium nitrite to give N-nitroso-α-iminodiacetonitrile. The nitroso compound is then filtered off, dried, and recrystallized twice from ethyl acetate/petroleum ether. Only after this purification is it reacted with sodium methylate solution under nitrogen at room temperature for 16 hours. Working up the mixture gives 2-amino-6-methoxypyrazine:

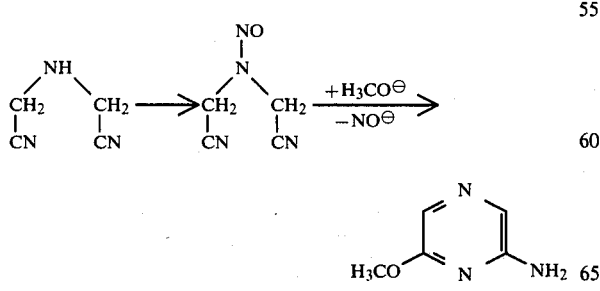

2-Amino-6-ethoxy-pyrazine is also prepared by a similar method. It should be pointed out that -iminodiacetonitrile itself does not undergo cyclization under the above conditions, and that the formation of the pyrazine ring is made possible only by the combined effect of the N-nitroso and nitrile groups on the acidity of the protons α to the nitrile group.

We have found that mixtures of 2-aminopyrazines of the formula Ia

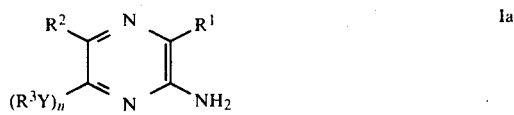

and of pyrazines of the formula Ib

where the individual radicals $R^1$ and $R^2$ can be identical or different and are each hydrogen or an aliphatic, cycloaliphatic, araliphatic or aromatic radical, $R^3$ is an aliphatic, cycloaliphatic, araliphatic or aromatic radical, Y is oxygen or sulfur, Z is halogen or a radical Y $R^3$, where Y and $R^3$ have the above meanings, and n is 0 or, when reaction c is carried out, may be 1, are advantageously obtained by cyclization of a dinitrile compound if an α-iminodiacetonitrile of the formula II

where $R^1$ and $R^2$ have the above meanings, is reacted (a) with a hydrogen halide of the formula III

where X is halogen, or
(b) with an alcohol and/or a thioalcohol of the formula IV

where Y and $R^3$ have the above meanings, and a hydrogen halide of the formula III

where X is halogen, or
(c) with an alcohol and/or a thioalcohol of the formula IV

where Y and $R^3$ have the above meanings, in the presence of an alkali metal compound and/or an alkaline earth metal compound.

We have furthermore found the novel 2-aminopyrazines of the formula Ia

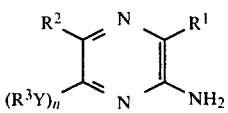

where the individual radicals $R^1$ and $R^2$ can be identical or different and are each hydrogen or an aliphatic, cycloaliphatic, araliphatic or aryl radical, $R^3$ is an aliphatic, cycloaliphatic, araliphatic or aromatic radical, Y is oxygen or sulfur and n is 0 or 1, and if $R^1$ and $R^2$ are each hydrogen, methyl or ethyl or a methyl radical which is substituted via nitrogen atoms or oxygen atoms or are each phenyl, then n is 1, or if $R^1$ and $R^2$ are each hydrogen, n is 1, Y is oxygen and $R^3$ is alkyl, then $R^3$ is alkyl of not less than 3 carbon atoms.

Where the starting materials shown are used, the reaction can be represented by the following equations:

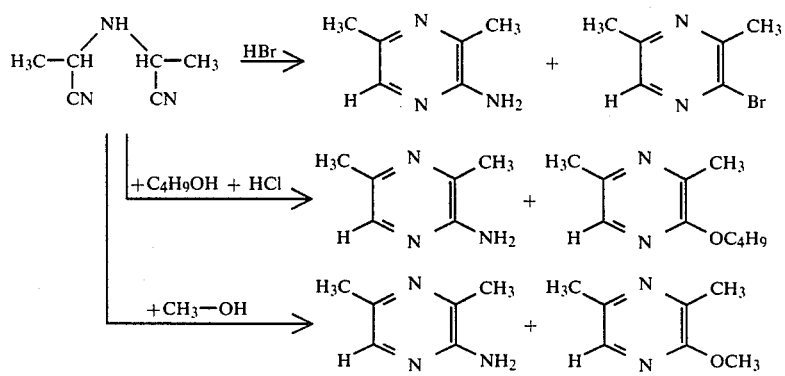

Compared with the processes described, the process according to the invention employs readily obtainable starting materials and gives mixtures of 2-aminopyrazines and pyrazines in very good yield by a simpler and more economical route. Compared with the publication in J. Org. Chem., the novel process saves a reaction stage and avoids the use of toxic nitrous acid and its nitrites. Compared to the publication in Chem. Ber., the starting materials according to the invention are easier to obtain. In view of the prior art, all these advantageous properties are surprising; it was to be expected that α-iminodiacetonitriles II would be unsuitable for a single-stage conversion to 2-aminopyrazines. Surprisingly, using process b, asymmetric α-iminodiacetonitriles Ii give end products I with substantial regiospecificity with regard to the radicals $R^1$ and $R^2$. For the purposes of the present invention, regiospecificity is the preference for one isomer over the others.

In view of, for example, U.S. Pat. No. 3,607,910, it is surprising that, when α- and α,α'-substituted starting materials II are used, procedure (b) gives high yields of the end products I and no significant amounts of substituted iminodiacetates.

The starting materials II can be prepared in a conventional manner, for example α-iminodipropionitrile II can be prepared by the reaction of ammonia with acetaldehyde and hydrocyanic acid, this reaction being described in German Laid-Open Application Dos No. 1,493,752. Preferably, symmetric starting materials II and the hitherto unobtainable asymmetric starting materials II are prepared by the procedure described in Ger-man Patent Application No. P 32 42 193.1; in this procedure, an aldehyde-cyanohydrin of the formula

is reacted with an aminonitrile of the formula

where $R^1$ and $R^2$ have the above meanings and can be identical or different. In the case of asymmetric and in particular of symmetric α-iminodiacetonitriles II, the reaction is advantageously carried out in the presence of a lower alkanol, using from 5 to 95% by weight, relative to the total amount of lower alkanol, of starting material IV. α-Iminodiacetonitriles II can also be prepared by reacting a haloacetonitrile of the formula VII

where $R^1$ and X have the above meanings, with an aminonitrile VI in the presence of an auxiliary base. The abovementioned general and subsequently mentioned preferred meanings of the radicals $R^1$, $R^2$ and X also apply to the preparation of the starting materials II. Preferably, from 1 to 2, in particular from 1 to 1.2, moles of starting material V or from 1 to 1.5, in particular from 1 to 1.2, moles of starting material VII are employed per mole of starting material VI. The reaction is advantageously carried out at from 0° to 100° C., preferably from 20° to 60° C., under atmospheric or superatmospheric pressure, either continuously or batchwise, advantageously in the presence of from 1 to 2 moles of total water (water of reaction + additional water) per mole of starting material VI. Advantageous auxiliary bases are tertiary amines; the amine is advantageously used in an amount of from 1 to 2 equivalents, based on substance VII. Where substances VII are used, it is also possible to employ inert organic solvents, eg. ethers, advantageously in an amount of from 100 to 10,000% by weight, based on starting material VII.

The starting materials can be reacted in stoichiometric amounts, or either of the components can be used in excess; preferably from 1.5 to 6, in particular from 2 to 5, moles of starting material III are employed per mole of starting material II in the case of process (a), from 1.5 to 6, in particular from 2 to 5, moles of starting material III and/or from 0.1 to 10, in particular from 0.5 to 3, moles of starting material IV are employed per mole of starting material II in the case of process (b), and from 5 to 50, in particular from 10 to 25, % by weight, based on starting material IV, of starting material II are employed in the case of process (c). Preferred starting materials II, III and IV, and accordingly preferred end products Ia and Ib, are those of the formulae where $R^1$ and $R^2$ can be identical or different and are each alkyl of 1 to 20, preferably 1 to 8, in particular 1 to 4, carbon atoms or alkenyl of 2 to 20, preferably 2 to 8, in particular 2 to 4, carbonatoms (or, in the case of process (c), an alkyl radical of 1 to 20, preferably 1 to 8, in particular 1 to 4, carbon atoms which is substituted by alkoxy and-/or alkylthio, each of which is advantageously of 1 to 4 carbon atoms, or, in the case of processes (a) and (b), a corresponding alkyl radical which is substituted by halogen, preferably chlorine, bromine or fluorine) or cycloalkyl of 5 to 8 carbon atoms, alkylaryl or aralkyl of 7 to 12 carbon atoms or phenyl, and one of the radicals $R^1$ and $R^2$ may furthermore be hydrogen, $R^3$, in the case of process (b), is alkyl which is of 1 to 20, preferably 1 to 8, in particular 1 to 4, carbon atoms and is unsubstituted or substituted by halogen or carbalkoxy of 2 to 4 carbon atoms, and, in the case of process (c) is alkyl of 1 to 8, in particular 1 to 4, carbon atoms, Y is oxygen or sulfur, Z is bromine, chlorine or a radical $-YR^3$, where Y and $R^3$ have the above meanings, and n is 0 or, if reaction (c) is carried out, may be 1, and X is bromine or chlorine. The above radicals may be further substituted by groups which are inert under the reaction conditions, for example alkyl, alkoxy or alkylthio groups, each of 1 to 4 carbon atoms. Mixtures of alcohols and thioalcohols may also be used.

Where the reaction is carried out using asymmetric starting materials II, both the end product Ia and the end product Ib are obtained in the form of their isomers in the 3- and 5-positions, for example the isomers of the formulae

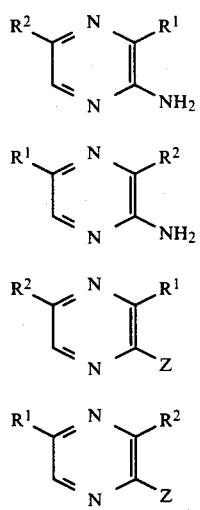

In process (b), the isomer ratio of Iaa and Iab or Iba and Ibb is generally 20–4, in particular 15–10, moles bf compound with a carbon-rich substituent $R^1$ in the 3-position to 1 mole of compound with a relatively carbon-poor substituent $R^2$ in the 5-position, $R^1$ and $R^2$ being different and each being an aliphatic or araliphatic radical or hydrogen.

The ratio of the end products I in the mixture is in general from 50 to 1, in particular from 50 to 2, moles of Ia per mole of Ib in process (a), from 6 to 1, in particular from 3 to 2, moles of Ia per mole of Ib in process b (alcohols), from 50 to 2, in particular from 16 to 4, moles of Ia per mole of Ib in process b (thioalcohols) and from 100 to 1, in particular from 10 to 2, moles of Ia per mole of Ib in process (c).

Examples of suitable starting materials II are $\alpha,\alpha'$-iminodiacetonitriles which are substituted symmetrically in the $\alpha$- and $\alpha'$-positions to the nitrile groups by methyl, phenyl, benzyl, cyclohexyl, ethyl, propyl, isopropyl, butyl, sec.-butyl or isobutyl; $\alpha'$-unsubstituted iminodiacetonitrile; $\alpha,\alpha'$-iminodiacetonitriles which are unsubstituted in the $\alpha$-position to a nitrile group but are substituted in the $\alpha'$-position to the other nitrile group by methyl, ethyl, propyl, isopropyl, butyl, isobutyl, sec.-butyl, cyclohexyl, benzyl or phenyl; and $\alpha,\alpha'$-iminodiacetonitriles which are asymmetrically substituted $\alpha$ and $\alpha'$ to the nitrile groups by the above groups.

Advantageous starting materials III are hydrobromic acid and hydrochloric acid; preferred starting materials IV are methyl alcohol and ethyl alcohol in the case of (c) and propyl alcohol, butyl alcohol, isobutyl alcohol, sec.-butyl alcohol, 2-methylbutyl alcohol and 2-chloroethyl alcohol in the case of (b), the corresponding thioalcohols also being preferred. In process (a), hydrobromic acid is particularly advantageous. The hydrogen halides can, if desired, also be used as a mixture with sulfonic acids, in particular aliphatic sulfonic acids of 1 to 4 carbon atoms.

The reaction is expediently carried out at from 0° to 100° C., in the case of reaction (a) advantageously at from 40° to 80° C., in the case of reaction (b) advantageously at from 20° to 80° C., preferably from 30° to 70° C., and in the case of reaction (c) advantageously at from 0° to 80° C., preferably from 20° to 60° C., under reduced, atmospheric or superatmospheric pressure, either batchwise or continuously. The reaction time is advantageously from 0.1 to 200, preferably from 3 to 48, hours. If required, organic solvents which are inert under the reaction conditions are used. Examples of suitable solvents are aromatic hydrocarbons, eg. toluene, benzene, ethylbenzene or o-, m- or p-xylene, aliphatic and cycloaliphatic hydrocarbons, eg. heptane, cyclohexane, methylcyclohexane of decalin, halohydrocarbons, in particular chlorohydrocarbons, eg. 1,1,2,2- or 1,1,1,2-tetrachloroethane, 1,2-dichloropropane, methylene chloride, dichlorobutane, n-propyl bromide, butyl bromide, chloroform, carbon tetrachloride, 1,1,2-trichloroethane, pentachloroethane, 1,2-dichloroethane, 1,1-dichloroethane, n-propyl chloride, 2-butyl chloride isobutyl chloride, chlorobenzene, bromobenzene, o-, p- or m-dichlorobenzene, o-, p- or m-dibromobenzene, o-, m- or p-chlorotoluene or 1,2,4-trichlorobenzene (also preferred in the case of reaction (a), ethers, eg. ethyl propyl ether, n-butyl ethyl ether, di-n-butyl ether, diisobutyl ether, diisoamyl ether, diisopropyl ether, diethyl ether or dioxane (preferred in the case of reaction (b) using hydrochloric acid), mercaptans, eg. butylmercaptan, octylmercaptan or dodecylmercaptan, and appropriate mixtures. Advantageously, the solvent is used in an amount of from 40 to 10,000, preferably from 50 to 1,500, percent by weight, based on starting material II. If appropriate, starting material IV itself may be used as the solvent; in such cases, it is advantageous to supplement the above amounts of starting materials IV by an amount of the latter equivalent to the amount of solvent omitted. In the case of process (c), an additional organic solvent is not generally used. Owing to the high solubility of hydrogen chloride in alcohols and ethers, the reaction can be carried out under atmospheric pressure in such cases. In dioxane/alcohol(thioalcohol) mixtures as used in process (b), particularly homogeneous salt mixtures are formed, and these give high yields of pyrazines Ia and Ib. Where a thioalcohol IV is used in process (b), a particularly high molar ratio of Ia to Ib is obtained. However, it is then advantageous, where working up is carried out in an aqueous medium, to replace the solvent with one which is water-immiscible. Hence, it is also very advantageous to carry out the process in pure isobutanol, in which case the solvent need not be changed.

Reaction (c) is carried out in the presence of an auxiliary base, advantageously in catalytic amounts, expediently in an amount of from 0.1 to 2, preferably from 0.2 to 0.6, equivalents per mole of starting material II. The auxiliary bases are alkaline earth metal compounds and in particular alkali metal compounds, advantageously alcoholates, mercaptides, hydroxides or cyanides, or mixtures of these. Examples of suitable basic compounds are potassium hydroxide, sodium hydroxide, potassium carbonate, sodium carbonate, lithium hydroxide, calcium hydroxide, calcium oxide, barium oxide, magnesium hydroxide, sodium cyanide, sodium methanethiolate, sodium ethanethiolate, potassium methanethiolate, potassium ethanethiolate, potassium cyanide, sodium methylate, sodium propylate, potassium methylate, potassium ethylate, potassium n-propylate and potassium diethyleneglycolate.

Reaction (a-c) can be carried out as follows: (a) a mixture of starting materials II and III or (b) a mixture of starting materials II, III and IV or (c) a mixture of starting materials II and IV and an alkali metal compound, in the presence or absence of an organic solvent, is kept at the reaction temperature for the reaction time, and the end product is then isolated from the reaction mixture in a conventional manner. For example, end product Ia can be separated from end product Ib by fractional distillation after neutralization. In the case of processes (a) and (b), the working up of the reaction mixture advantageously begins with the neutralization of the excess acid and the liberation of the pyrazine salts by means of an alkali, preferably sodium hydroxide solution. After extraction of the aqueous phase with, for example, one of the above organic solvents, the combined organic phases are advantageously worked up by distillation.

The resulting end products Ib in which Z is halogen are the 2-halopyrazines of the formula

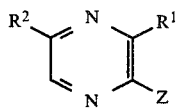
Ib which are relatively readily volatile and hence easy to isolate, and which can also be converted to the 2-amino compounds by the action of ammonia using a conventional method. Process (a) is advantageous for the preparation of unsubstituted end products I ($R^1=R^2=H$), while process (b) is advantageous for the preparation of end products I which are asymmetrically or symmetrically substituted in the 3- and 5-positions or aliphatically substituted only in the 3-position. Process (b) with thioalcohols is advantageously used for reacting the monosubstituted α-iminodiacetonitriles II (where $R^1$ or $R^2$ is H) which undergo cyclization much less readily. In such cases, particularly high total yields of pyrazines can be obtained by a combined reaction with an alcohol and a thioalcohol, using process (b).

Process (c) is particularly advantageous when using starting materials II having substituents in the 3- and 5-positions ($R^1=R^2$). Starting materials II which contain alkoxy groups and/or α-branched or α'-branched alkyl groups (branching or alkoxy group in the 1-position of the substituent=β-position), eg. isopropyl groups, are advantageously used for the preparation of 6-substituted end products Ia (n=1) by process (c). In these cases, in addition to the end products Ia (n=0) and Ib, the principal product formed is end product Ia (n=1) of the formula

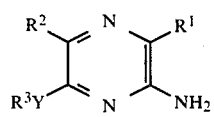

where $R^1$, $R^2$, $R^3$ and Y have the above meanings. Cleavage of an alkoxy group of radical $R^1$ or $R^2$ may take place during this reaction. For example, the following reactions may occur:

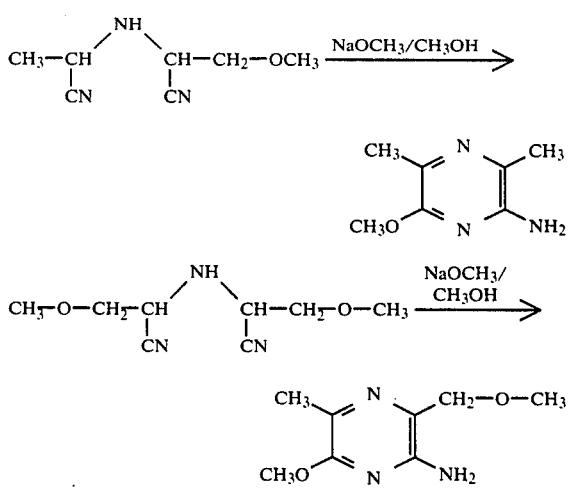

The 2-aminopyrazines and pyrazines obtainable by the process of the invention are useful starting materials for the preparation of dyes, fungicides, bactericides, textile assistants and scents. 2-Amino-3,5-dialkylpyrazines are intermediates for folic acid derivatives and 2-halopyrazines are intermediates for flavorings, scents and active ingredients in crop protection or drugs. Regarding the use of these compounds, reference may be made to the above German Laid-Open Application and to Ullmanns Encyklopädie der technischen Chemie (4th edition), volume 7, page 385 and volume 20, pages 528 and 529.

In a preferred form for use, the resulting end products Ia, in pure or crude form, are converted by the procedure described in German Patent Application No. P 32 42 266.0 to 2-halopyrazines or 2-cyanopyrazines of the formula

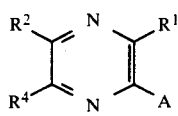   Ic by reaction at from $-50°$ to $+50°$ C.

(1a) with an alkali metal nitrite or an alkyl nitrite in the presence of water and/or an organic solvent and (1a1) with tetrafluoroboric acid or (1a2) a hydrohalic acid of the formula

   III in the form of a 10–80 percent strength by weight solution, using from 1 to 5 moles of starting material III per mole of substance Ia, or (1b) with a nitrosyl halide in the presence of an organic solvent which is inert under the reaction conditions, and, if desired, by reaction of the resulting 2-halopyrazines of the formula

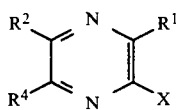   VIII with copper cyanide and, if required, an alkali metal cyanide and/or an alkaline earth metal cyanide at from $80°$ to $200°$ C. $R^1$, $R^2$, $R^3$, Y and Z have the above general and preferred meanings, and A is halogen, preferably chlorine, bromine or fluorine, or cyano, and $R^4$ is hydrogen or a radical $R^3Y$.

Preferred starting materials III are hydrochloric acid and hydrobromic acid. The nitrosyl halides used are those of the formula

   IX

Preferred alkali metal nitrites are sodium nitrite and potassium nitrite. Preferred alkyl nitrites are those of the formula

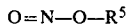   X where $R^5$ is alkyl of 1 to 6 carbon atoms, advantageously amyl nitrite, ethyl nitrite or neopentyl nitrite. Process 1a1 (tetrafluoric acid) is advantageously carried out using an organic solvent or, preferably, using a mixture of additional water with an organic solvent. Process 1a2 can be carried out using an organic solvent or, if appropriate, a mixture containing additional water, and is advantageously carried out in an aqueous medium. Starting materials IX can be replaced by the reaction mixtures used for their preparation, eg. from NO and a halogen, in particular bromine.

The starting materials can be reacted in stoichiometric amounts, or one or other of the components can be used in excess; preferably from 1 to 3, in particular from 1.05 to 1.2, moles of alkali metal nitrite or alkyl nitrite and preferably from 1 to 3, in particular from 1.05 to 1.2, moles of $HBF_4$, or from 1 to 3, in particular from 1.05 to 1.5, moles of starting material IX, are used per mole of substance Ia. From 1 to 5, preferably from 2 to 4, moles of starting material III are used per mole of substance Ia. The reaction (1a) or (1b) is carried out at from $-50°$ to $+50°$ C., advantageously at from $-30°$ to $+40°$ C., in particular from $-20°$ to $+25°$ C., in the case of process (1a), and advantageously at from $-25°$ to $+40°$ C., in particular from $-25°$ to $0°$ C., in the case of process (1b), under reduced, atmospheric or superatmospheric pressure, either batchwise or continuously. A solvent is used for processes (1a) and (1b). Water is introduced into the reaction wholly or partially in the form of a solution of the acid III, and advantageously in the form of a solution of the alkali metal nitrite. the solvent used depends on the process, and suitable organic solvents are in general halohydrocarbons (preferably for (1b), in particular chlorohydrocarbons, ethers (preferably for (1a), alkanols and cycloalkanols (preferably for (1a), sulfoxides and sulfones, esters (preferably in the absence of additional amounts of water), carboxylic acids of 1 to 6 carbon atoms (preferably for (1a), and mixtures of these. Advantageously, the organic solvent and/or additional water are used in an amount of from 50 to 5,000, preferably from 100 to 1,000, % by weight, based on substance Ia. Some or all of the solvent may also be employed in the form of the corresponding solution of the starting material, eg. of tetrafluoboric acid. Starting material III is used in the form of a 10–80, preferably 30–70, percent strength by weight solution. The reaction time is advantageously from 0.2 to 5 hours. In a preferred embodiment, nitrosyl bromide is used in a single-vessel process. First the bromine, which is initially taken in a suitable solvent, eg. one of the above, is converted to NOBr by passing in NO at from $+10°$ C. to $-40°$ C., preferably from $-10°$ C. to $-20°$ C., and thereafter the 2-aminopyrazine Ia, dissolved in one of the above solvents, is metered in at the same temperature.

Substance VIII can be reacted with copper cyanide alone, either in a stoichiometric amount or advantageously in excess; advantageously from 1 to 2, preferably from 1.05 to 1.5, moles of copper cyanide are used per mole of starting material VIII. Some of the copper cyanide can be replaced with an alkali metal cyanide and/or an alkaline earth metal cyanide, advantageously lithium cyanide, calcium cyanide or barium cyanide, preferably sodium cyanide or potassium cyanide; advantageously from 1 to 3, preferably from 1.1 to 1.5, moles of alkali metal cyanide and/or alkaline earth metal cyanide are used per mole of starting material VIII. A mixture containing from 10 to 50, preferably from 15 to 25, mole %, based on all cyanides, of copper cyanide is advantageous. The reaction is carried out at from $80°$ to $200°$ C., preferably from $120°$ to $160°$ C., under reduced, atmospheric or superatmospheric pressure, either continuously or batchwise. It is advantageous to use heterocyclic solvents which are inert under the reaction conditions, advantageously in an amount of from 100 to 5,000, preferably 200 to 1,000, % by weight, based on substance Ia. The reaction time is from 1 to 12 hours.

As a result of this elegant 3-stage procedure, ie. the preparation of starting material II, the conversion of this to end product Ia and the conversion of the latter to end product Ic by the above procedures, a large number of synthesis routes in the abovementioned industrial fields, eg. for folic acid compounds, surprisingly become possible or become more economical and simpler.

In the Examples which follow, the yield is based on starting material II converted.

Process (a) with hydrogen chloride and hydrogen bromide

EXAMPLES 1-4

The α-iminodiacetonitriles listed in Table 1 were dissolved or suspended in a solvent, and the solution or suspension was gassed with hydrogen halide at from 1° to 5° in the course of 1 hour in an autoclave equipped with an anchor stirrer. The mixture was then heated to the stated maximum temperature and allowed to continue reacting. The pressure was then let down, after which the mixture was brought to pH 8 with sodium hydroxide solution, the organic phase was separated off, the aqueous phase was extracted exhaustively with methylene chloride, and the combined organic phases were distilled.

Details of the synthesis are shown in Table 1, while the most important physical properties of the pyrazines isolated are summarized in Tables 5 and 6.

clave under 1 bar: Example 10) in the course of 60 minutes, and the mixture was brought to the reaction temperature (T max) over a period of 60 minutes. The reaction was monitored by potentiometric titration of the excess hydrochloric acid. When the conversion remained constant, the mixture was brought to pH 8 with 20% strength by weight sodium hydroxide solution, the organic phase was separated off and the aqueous phase was extracted several times with isobutanol. The combined organic phases were evaporated down under reduced pressure at 60° C., and the residue was freed from remaining non-volatile constituents under 0.5 mbar and at a bottom temperature as high as 160° C. The distillate, which crystallizes readily, was recrystallized from diisopropyl ether, and the mother liquor was evaporated down until it was free of solvent. The remaining oil was analyzed by gas chromatography and fractionally distilled.

The mixture of 2-amino-3,5-dimethylpyrazine (Examples 7-10) with 2-isobutoxy-3,5-dimethylpyrazine was worked up by extraction with water and subsequent purification of the 50% strength by weight aqueous solution with steam (2-isobutoxy-3,5-dimethylpyrazine is readily volatile in the presence of steam).

Details of the synthesis are shown in Table 2, while the most important physical properties of the pyrazines isolated are summarized in Tables 5 and 6.

TABLE 1

Cyclization of iminodiacetonitriles II by process a

| Example | Amount in g | Iminodiacetonitrile II $R^1$ | $R^2$ | Solvent | g/mole II | Hydrogen halide | mole/mole of II | Maximum temperature °C. | Maximum pressure bar | Time at T max. (hours) | Yield (% of theory) of the end products Ib | Ia +Ib |
|---|---|---|---|---|---|---|---|---|---|---|---|---|
| 1 | 95 | H | H | $CH_2ClCH_2Cl$ | 650 | HBr | 3.2 | 80 | 7.2 | 6 | 45 | Br 1   46 |
| 2 | 123 | $CH_3$ | $CH_3$ | $CH_2ClCH_2Cl$ | 650 | HBr | 3.2 | 50 | 1.2 | 6 | 63 | Br 4   67 |
| 3 | 123 | $CH_3$ | $CH_3$ | $CH_2Cl_2$ | 800 | HBr / HCl | 1.0 / 2.4 | 50 | 2.2 | 6 | 20 | Cl 10   33 Br 3 |
| 4 | 68.5 | $C_2H_5$ | $CH_3$ | $CH_2Cl$—$CH_2Cl$ | 650 | HBr | 3.2 | 50 | 1 | 6 | Iaa 32 Iab 25 | Br 3   60 |

Process (b) with alcohol

EXAMPLES 5-18

The substituted α-iminodiacetonitriles II listed in Table 2 were dissolved in the stated solvent, and the stated alcohol IV was added. Not less than 2.6 moles of HCl gas per mole of starting material II were then passed into this solution at 25° C. (40° C.; in an auto-

TABLE 2

Process (b) with alcohol/cyclization of α-iminodiacetonitriles II to give 2-amino-3,5-dialkylpyrazines Ia

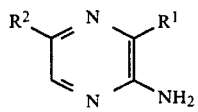

2-Alkoxy-3,5-dialkylpyrazines Ib2

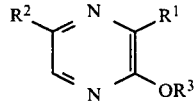

| Example | Amount in g | α-Iminodiacetonitrile II $R^1$ | $R^2$ | Solvent | g/mole of starting material II | $R^3OH$ | mole/mole of starting material II | HCl mole/mole of starting material II | Maximum temperature (°C.) | Time at T max (hours) | Yields (% of theory) of end products Ia | Ib2 | Ia + Ib2 |
|---|---|---|---|---|---|---|---|---|---|---|---|---|---|
| 5 | 123 | $CH_3$ | $CH_3$ | Dioxane | 292 | n-Propanol | 1.0 | 2.6 | 40 | 6 | 28 | 11 | 39 |
| 6 | " | " | " | " | 241 | n-Butanol | 1.5 | 3.2 | 40 | 3 | 38 | 17 | 55 |
| 7 | " | " | " | " | 241 | i-Butanol | 1.5 | 3.2 | 40 | 5.5 | 49 | 28 | 77 |
| 8 | 369 | " | " | Diisopropyl-ether | 148 | " | 2.0 | 3.2 | 50 | 3.5 | 54 | 29 | 83 |
| 9 | 123 | " | " | — | — | " | 4.8 | 3.2 | 50 | 7 | 48 | 28 | 76 |
| 10 | " | " | " | 1,2-Dichloro-ethane | 650 | " | 1.0 | 3.2 | 50 | 6 | 59 | 29 | 88 |
| 11 | " | " | " | — | — | 3-Methyl-butanol | 4.0 | 3.2 | 40 | 5.5 | 30 | 22 | 52 |

TABLE 2-continued

Process (b) with alcohol/cyclization of α-iminodiacetonitriles II
to give 2-amino-3,5-dialkylpyrazines Ia

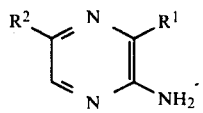

2-Alkoxy-3,5-dialkylpyrazines Ib2

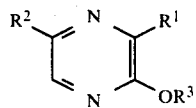

| Example | Amount in g | α-Iminodiacetonitrile II R¹ | R² | Solvent | g/mole of starting material II | R³OH | mole/mole of starting material II | HCl mole/mole of starting material II | Maximum temperature (°C.) | Time at T max (hours) | Yields (% of theory) of end products Ia | Ib2 | Ia + Ib2 |
|---|---|---|---|---|---|---|---|---|---|---|---|---|---|
| 12 | " | " | " | Dioxane | 176 | 2-Methyl-butanol | 2.0 | 3.2 | 40 | 4 | 54 | 22 | 76 |
| 13 | " | " | " | " | 222 | 2-Ethyl-hexanol | 1.0 | 3.2 | 40 | 4 | 46 | 20 | 66 |
| 14 | " | " | " | " | 191 | Chloro-ethanol | 1.0 | 2.6 | 50 | 6.5 | 55 | 10 | 65 |
| 15 | " | " | " | — | — | Butyl glycolate | 3.0 | 3.2 | 40 | 5 | 44 | 1 | 44–45 |
| 16 | " | " | " | Dioxane | 217 | Ethoxy-ethanol | 1.5 | 3.2 | 40 | 5 | 57 | 21 | 78 |
| 17 | 96 | C₂H₅ | " | " | 163 | i-Butanol | 1.5 | 3.2 | 40 | 6.5 | 44¹ | 21 | 65 |
| 18 | 151 | " | C₂H₅ | " | 204 | " | 2.0 | 5.1 | 40 | 4 | 43 | 19 | 62 |

¹X-ray structure determination

Process (b) with thiols

EXAMPLES 19–35

The substituted α-iminodiacetonitriles II listed in Table 3 were dissolved in the stated solvent, and the stated mercaptan was added. HCl gas was passed into this solution in the course of 60 minutes (in an autoclave: Example 30). In Examples 25 and 26, some of the HCl was replaced with methanesulfonic acid or hydrogen bromide. Thereafter, the mixture was brought to the reaction temperature (T max) in the course of 60 minutes, and was allowed to react while stirring vigorously (the mixtures were in general pasty). The progress of the reaction was monitored by potentiometric titration of the excess acid or by thin-layer chromatography.

When the conversion remained constant, the mixture was brought to pH 8.0 with 20% strength by weight sodium hydroxide solution, the organic phase was separated off and the aqueous phase was extracted several times with isobutanol. The combined organic phases were evaporated down under reduced pressure at 60° C., and the residue was freed from remaining non-volatile constituents under 0.5 mbar and at a bottom temperature as high as 160° C. The distillate, which generally crystallizes readily, was recrystallized or was purified by fractional distillation. It was analyzed by gas chromatography. Details of the synthesis are shown in Table 3, while the most important physical properties of the pyrazines I isolated are summarized in Tables 5 and 6.

TABLE 3

Process b with thiols/cyclization of α-iminodiacetonitriles II to give
2-aminopyrazines Ia 2-alkylmercaptopyrazines (Y = S) (Ib1)
2-alkoxypyrazines (Y = O) (Ib2) 2-halo-3,5-dialkylpyrazines (Ib3)

| Example | Amount in g | α-Iminodiaceto-nitrile II R¹ | R² | Solvent | g/mole of starting material II | R³SH | mole/mole of starting material II | HCl mole/mole of starting material II |
|---|---|---|---|---|---|---|---|---|
| 19 | 65.4 | CH₃ | H | Dioxane | 400 | n-C₄H₉SH | 0.5 | 2.9 |
| 20 | 75.5 | i-C₄H₉ | H | Dichloro-ethane | 650 | " | " | 3.2 |
| 21 | 123 | C₂H₅ | H | Dioxane | 307 | " | " | 3.3 |
| 22 | 43 | Phenyl | H | " | 460 | " | " | 3.5 |
| 23 | 123 | CH₃ | CH₃ | " | 321 | C₂H₅SH | " | 3.0 |
| 24 | 123 | " | " | " | 307 | n-C₄H₉SH | " | 2.9 |
| 25 | 123 | " | " | " | " | " | " | 1² |
| 26 | 123 | " | " | " | " | " | " | 1.1³ |
| 27 | 123 | CH₃ | CH₃ | Dioxan | 284 | n-C₄H₉SH | 0.75 | 3.2 |
| 28 | 123 | " | " | i-Butanol | 307 | i-C₄H₉SH | 0.5 | 3.2 |
| 29 | 123 | " | " | " | 410 | Octanethiol | 0.25 | 3.2 |
| 30 | 123 | " | " | 1,2-Di-chloroethane | 650 | n-C₄H₉SH | 0.5 | 3.2 |
| 31 | 137 | C₂H₅ | " | Dioxan | 307 | i-C₄H₉SH | 0.5 | 3.2 |
| 32 | 226.5 | i-C₃H₇ | " | " | " | n-C₄H₉SH | 0.5 | 3.5 |
| 33 | 165.6 | 2-Ethyl- | " | " | " | " | " | 3.3 |

TABLE 3-continued

Process b with thiols/cyclization of α-iminodiacetonitriles II to give
2-aminopyrazines Ia 2-alkylmercaptopyrazines (Y = S) (Ib1)
2-alkoxypyrazines (Y = O) (Ib2) 2-halo-3,5-dialkylpyrazines (Ib3)

|    |      | pentyl |    |    |     |    |    |     |
|----|------|--------|----|----|-----|----|----|-----|
| 34 | 59.7 | Benzyl | "  | "  | 675 | "  | "  | 5.3 |
| 35 | 18.5 | Phenyl | "  | "  | 400 | "  | "  | 3.2 |

| Example | Maximum temperature °C. | Time at T max (hours) | Yield (% of theory) of end product Ia | Ib1 | Total pyrazines I | Con- version (%) |
|---|---|---|---|---|---|---|
| 19 | 30 | 5 | Iaa 28[1] Iab 3 | 6 | 37 | 80 |
| 20 | 50 | 5 | 74 | 2 | 76 | |
| 21 | 40 | 5 | 44 | 4 | 48 | |
| 22 | 40 | 5,5 | Iaa 18 Iab 24 | 3 | 45 | |
| 23 | 40 | 9 | 64 | 8 | 72 | |
| 24 | 60 | 5 | 70 | 7 | 77 | |
| 25 | 50 | 13 | 35 | 4 | 39 | 85 |
| 26 | 50 | 8 | 32 | 8 4 Ib3 (X = Br) | 44 | |
| 27 | 40 | 5.5 | 63 | 13 | 76 | |
| 28 | 50 | 8 | 55 | Ib2 32 | 87 | |
| 29 | 60 | 3 | 44 | 30 | 74 | |
| 30 | 50 | 6 | 60 | 5 + Ib3 (X = Cl)1 | 66 | |
| 31 | 40 | 6 | Iaa 66 Iab 4 | | | |
| 32 | 40 | 9 | 40 | | | 90 |
| 33 | 40 | 5 | 50 | | | 70 |
| 34 | 45 | 6 | 42[1] | | | |
| 35 | 40 | 6 | Iaa 15 Iab 35 | | | |

[1]X-ray structure determination
[2]+2.2 moles of $CH_3SO_3H$
[3]+1 mole of HBr

Process c

EXAMPLES 36–44

The substituted α-iminodiacetonitriles II listed in Table 4 were dissolved in methanol to give a 15% strength by weight solution, and 0.5 mole of an auxiliary base per mole of starting material II was added at 22° C. The progress of the reaction was monitored by thin-layer chromatography. When the reaction was complete, the mixture was brought to pH 8.0 with concentrated hydrochloric acid, and the solvent, together with hydrocyanic acid liberated, was separated off under slightly reduced pressure. 100 g of water per mole of dinitrile II employed were added to the residue, and the mixture was extracted with methylene chloride. The extracts were evaporated down, and the residues were distilled. The pyrazine mixture distilled over at from 100° to 120° C./0.5 mbar. The alkoxypyrazines were substantially more readily volatile, so that their isolation presented no difficulties. The distillates were analyzed by gas chromatography, and the principal components were isolated by fractional distillation or by recrystallization from diisopropyl ether, with or without the addition of hexane. The pure pyrazines were characterized by elemental analysis and their NMR and UV spectra. Details of the synthesis are shown in Table 4, while the most important physical properties of the pure pyrazine derivatives isolated are summarized in Tables 5 and 6.

TABLE 4

Process (c)/cyclization of α-iminodiacetonitriles II to give
2-aminopyrazines Ia
2-alkoxypyrazines Ib
2-amino-6-alkoxypyrazines Ic

| Example | Amount in g | α-Iminodiacto- nitrile II R[1] | R[2] | R[3]OH | Auxiliary base | Temperature °C. | Time (days) | Yield (% of theory) Ia | Ib | Ic |
|---|---|---|---|---|---|---|---|---|---|---|
| 36 | 123 | $CH_3$ | $CH_3$ | $CH_3OH$ | $NaOCH_3$ | 40 | 3 | 48 | 10 | 24 |
| 37 | 137 | $C_2H_5$ | $CH_3$ | " | " | " | 5 | Iaa 20 Iab 14 | Iba 10 Ibb 3 | — |
| 38 | 15.3 | $CH_3OCH_2$ | " | " | $NaOCH_3/KCN$ (1:1) | 22 | 4 | | | 40 |
| 39 | 16.7 | $C_2H_5OCH_2$ | " | " | $NaOCH_3$ | 22 | 4 | | | 44 |
| 40 | 30.2 | $CH(CH_3)_2$ | " | " | " | 40 | 6 | | | 22 |
| 41 | 10 | 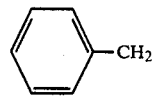$-CH_2$ | " | " | " | 22 | 4 | Iaa 20 Iab 11 | Iba 16 Ibb 6 | — |
| 42 | 15.1 | $C_2H_5$ | $C_2H_5$ | " | " | 40 | 6 | 30 | | — |
| 43 | 18.3 | $CH_3OCH_2$ | $CH_3OCH_2$ | " | $LiOCH_3$ | 22 | 3 | | | 49[1] |

TABLE 4-continued

Process (c)/cyclization of α-iminodiacetonitriles II to give
2-aminopyrazines Ia
2-alkoxypyrazines Ib
2-amino-6-alkoxypyrazines Ic

| Example | Amount in g | α-Iminodiaceto-nitrile II R¹ | R² | R³OH | Auxiliary base | Temperature °C. | Time (days) | Yield (% of theory) Ia | Ib | Ic |
|---|---|---|---|---|---|---|---|---|---|---|
| 44 | 18.3 | " | " | " | NaOH | " | 2 | | | 42 |

[1] X-ray structure determination

TABLE 5

| Example | Formula | Mp. (°C.) | Purity, % by weight | UV spectra in methanol max.₁ | E₁ | max.₂ | E₂ |
|---|---|---|---|---|---|---|---|
| 1 | 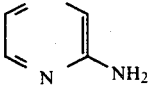 | 115–117 | 99.5 | 232 | 10415 | 316 | 6168 |
| 19 | 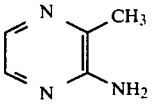 | 166–168 | 100 | 233 | 10360 | 316 | 6209 |
| 21 | 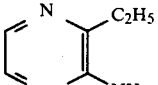 | 49–50 | 99.2 | 234 | 9962 | 319 | 6288 |
| 20 | 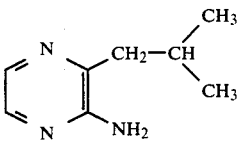 | 80–81 | 98.7 | 270 | 8449 | 335 | 7989 |
| 22 | 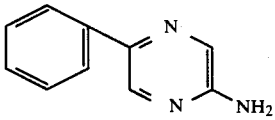 | 140–42 | 98.9 | 215 | 9506 | | |
| 23 | 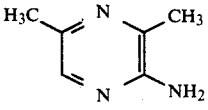 | 93–95 | 99.6 | 234 | 11107 | 324 | 6210 |
| 31 | 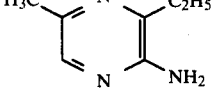 | 49–52 | 95.3 | 235 | 10605 | 325 | 6161 |
| 32 | 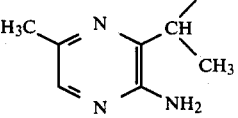 | 56–60 | 97.5 | 234 | 10828 | 323 | 6487 |
| 33 | 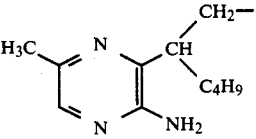 | 74–75 | 97 | 235 | 10787 | 327 | 6610 |

TABLE 5-continued

| Example | Formula | Bp. (°C./mbar) | $n_D^{20}$ | Purity, % by weight | max.₁ | E₁ | max.₂ | E₂ |
|---|---|---|---|---|---|---|---|---|
| 34 | (structure: H₃C–pyrazine–CH₂–Ph, NH₂) | | $n_D^{20}$ = 1.6125 | 97 | 234 | 10233 | 327 | 6427 |
| 35 | (structure: Ph–pyrazine–CH₃, NH₂) | 120–130 | | 98 | 275 | 15231 | 334 | 10106 |
| 18 | (structure: H₅C₂–pyrazine–C₂H₅, NH₂) | 47–48 | | 99.7 | 235 | 11677 | 324 | 6632 |
| 38 | (structure: H₃C–pyrazine–CH₃, CH₃O, NH₂) | 94–95 | | 97.2 | 236 | 11030 | 328 | 10528 |
| 43 | (structure: CH₃O–pyrazine–CH₂–OCH₃, NH₂) | 52–55 | | 96.3 | 243 | 11329 | 326 | 9719 |

| | | Bp. | | Purity, | UV spectra in methanol | | | |
|---|---|---|---|---|---|---|---|---|
| Example | Formula | (°C./mbar) | $n_D^{20}$ | % by weight | max.₁ | E₁ | max.₂ | E₂ |
| 36 | (structure: H₃C–pyrazine–CH₃, O–CH₃) | 74/20 | 1.5041 | 99.5 | | | | |
| 5 | (structure: H₃C–pyrazine–CH₃, O–C₃H₇) | 66/0.4 | | | | | | |
| 7 | (structure: H₃C–pyrazine–CH₃, O–CH₂–CH(CH₃)CH₃) | | 1.4840 | 98.8 | 216 | 11641 | 300 | 6899 |
| 12 | (structure: H₃C–pyrazine–CH₃, O–CH₂–CH(C₂H₅)CH₃) | | 1.4850 | 98.7 | 216 | 11485 | 300 | 6939 |
| 13 | (structure: H₃C–pyrazine–CH₃, O–CH₂–CH(C₄H₉)C₂H₅) | | 1.4826 | 97 | 216 | 11418 | 300 | 6752 |
| 16 | (structure: H₃C–pyrazine–CH₃, O–C₂H₄–OC₂H₅) | | 1.4890 | 96.8 | 215 | 10772 | 299 | 6590 |

TABLE 5-continued

| 28 |  | 1.5421 | 97.3 | 248 | 11640 | 322 | 7105 |
|---|---|---|---|---|---|---|---|

TABLE 6

| | | Bp. | | Purity, | UV spectra in methanol | | | |
|---|---|---|---|---|---|---|---|---|
| Example | Formula | (°C./mbar) | $n_D^{20}$ | % by weight | max.$_1$ | E$_1$ | max.$_2$ | E$_2$ |
| 17 | (structure) | 63–65/0.3 | | | | | | |
| 3 | 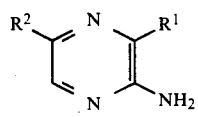 | 87/30 | 1.5269/9–10° C. | 99 | 211 | 9419 | 279 | 6954 |
| 2 | 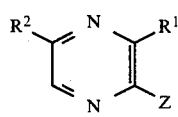 | 55/0.3 | 1.5590/7–8° C. | 99 | | | | |

We claim:

1. A process for the preparation of a mixture of a 2-aminopyrazine of the formula $$\underset{\text{Ia}}{R^2\diagdown N\diagup R^1 \atop N\diagdown NH_2}$$

with a pyrazine of the formula $$\underset{\text{Ib}}{R^2\diagdown N\diagup R^1 \atop N\diagdown Z}$$

where the individual groups $R^1$ and $R^2$ can be identical or different and each are hydrogen, alkyl of 1 to 20 carbon atoms or said alkyl substituted by halogen, alkenyl of 2 to 20 carbon atoms, cycloalkyl of 5 to 8 carbon atoms, alkylaryl or aralkyl of 7 to 12 carbon atoms or phenyl, Z is halogen when reaction (a) is carried out or the group $YR^3$, when reaction (b) is carried out, Y being oxygen or sulfur and $R^3$ being alkyl of 2 to 20 carbon atoms, or cycloalkyl or aralkyl of up to 8 carbon atoms, which process comprises:

cyclizing an α-iminodiacetonitrile of the formula

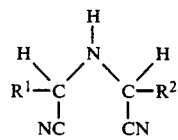

where $R^1$ and $R^2$ have the above meanings, by reaction (a) with a hydrogen halide of the formula

H—X     III where X is halogen, or (b) with an alcohol and/or a thioalcohol of the formula

HYR$^3$     IV where Y and $R^3$ have the above meanings, and a hydrogen halide of the formula

H—X     III where X is halogen.

2. A process as claimed in claim 1, wherein the reaction is carried out using from 1.5 to 6 moles of starting material III per mole of starting material II in the case of process (a), and from 1.5 to 6 moles of starting material III and/or from 0.1 to 10 moles of starting material IV per mole of starting material II in the case of process (b).

3. A process as claimed in claim 1, wherein the reaction is carried out using starting materials II, III and IV of the formulae where $R^1$ and $R^2$ can be identical or different and are each alkyl of 1 to 20 carbon atoms or said alkyl substituted by halogen, alkenyl of 2 to 20 carbon atoms, cycloalkyl of 5 to 8 carbon atoms, alkylaryl or aralkyl of 7 to 12 carbon atoms or phenyl, and one of the groups $R^1$ and $R^2$ may furthermore be hydrogen, and $R^3$, in the case of process (b) is alkyl of 2 to 20 carbon atoms or said alkyl substituted by halogen or carbalkoxy of 2 to 4 carbon atoms, Y is oxygen or sulfur, and X is bromine or chlorine, and each of $R^1$, $R^2$ and $R^3$ may be further substituted by alkyl, alkoxy or alkylthio, each of 1 to 4 carbon atoms.

4. A process as claimed in claim 1, wherein the reaction is carried out at from 0° to 100° C.

5. A process as claimed in claim 1, wherein the reaction (a) is carried out at from 40° to 80° C. and reaction (b) is carried out at from 20° to 80° C.

6. A process as claimed in claim 1, wherein the reaction is carried out using an organic solvent which is inert under the reaction conditions.

7. A process as claimed in claim 1, wherein reaction (a) is carried out at a temperature of from 0° to 100° C. using 1.5 to 6 moles of starting material III per mole of starting material II in the presence of an inert organic solvent.

8. A process as claimed in claim 1, wherein reaction (b) is carried out at a temperature of from 0° to 100° C. using 1.5 to 6 moles of starting material III and/or 0.1 to 10 moles of starting material IV per mole of starting material II.

* * * * *